(12) United States Patent
Seiler

(10) Patent No.: US 9,017,406 B2
(45) Date of Patent: Apr. 28, 2015

(54) DEVICE FOR COVERING AND/OR RECONSTRUCTING A BONE DEFECT SITE, AND METHOD FOR PRODUCTION THEREOF

(75) Inventor: Marcus Seiler, Stuttgart (DE)

(73) Assignee: ReOss GmbH, Filderstadt (DE)

( * ) Notice: Subject to any disclaimer, the term of this patent is extended or adjusted under 35 U.S.C. 154(b) by 109 days.

(21) Appl. No.: 13/579,626

(22) PCT Filed: Feb. 14, 2011

(86) PCT No.: PCT/DE2011/000131
§ 371 (c)(1),
(2), (4) Date: Sep. 11, 2012

(87) PCT Pub. No.: WO2011/100951
PCT Pub. Date: Aug. 25, 2011

(65) Prior Publication Data
US 2013/0006380 A1 Jan. 3, 2013

(30) Foreign Application Priority Data

Feb. 19, 2010 (DE) .......................... 10 2010 009 333
Oct. 21, 2010 (DE) .......................... 10 2010 049 809

(51) Int. Cl.
*A61F 2/02* (2006.01)
*A61F 2/28* (2006.01)
*A61L 31/14* (2006.01)

(52) U.S. Cl.
CPC .......... *A61L 31/148* (2013.01); *Y10T 29/49769* (2015.01); *A61L 31/14* (2013.01); *A61L 2430/02* (2013.01)

(58) Field of Classification Search
CPC .......... A61B 17/82; A61B 17/80; A61F 2/28
USPC .............. 623/11.11, 16.11, 18.11; 606/69–77; 660/280, 281
See application file for complete search history.

(56) References Cited

U.S. PATENT DOCUMENTS

| 4,816,339 A | 3/1989 | Tu et al. |
| 5,741,257 A | 4/1998 | Kirsch |
| 5,824,088 A * | 10/1998 | Kirsch ..................... 424/423 |

(Continued)

FOREIGN PATENT DOCUMENTS

| DE | 42 26 465 | 2/1993 |
| DE | 42 26 465 A1 | 2/1993 |

(Continued)

OTHER PUBLICATIONS

International Search Report of PCT/DE2011/000131, Jun. 21, 2011.

(Continued)

*Primary Examiner* — Jason-Dennis Stewart
(74) *Attorney, Agent, or Firm* — Collard & Roe, P.C.

(57) ABSTRACT

A device for covering and/or reconstructing a bone defect site and a method for producing a cap of a covering device for a bone defect site, wherein the device for covering and/or reconstructing a bone defect site consists of a cap (moulded shell, rigid shell, shaped body) and of at least one fixing means for fixing the cap on a bone. The cap is distinguished by having a dimensionally stable (rigid) nature, and a wall of the cap directed towards the bone defect or a wall of the cap directed away from the bone defect corresponds to the shape of the regenerated bone.

19 Claims, 4 Drawing Sheets

(56) References Cited

U.S. PATENT DOCUMENTS

Figure 1:
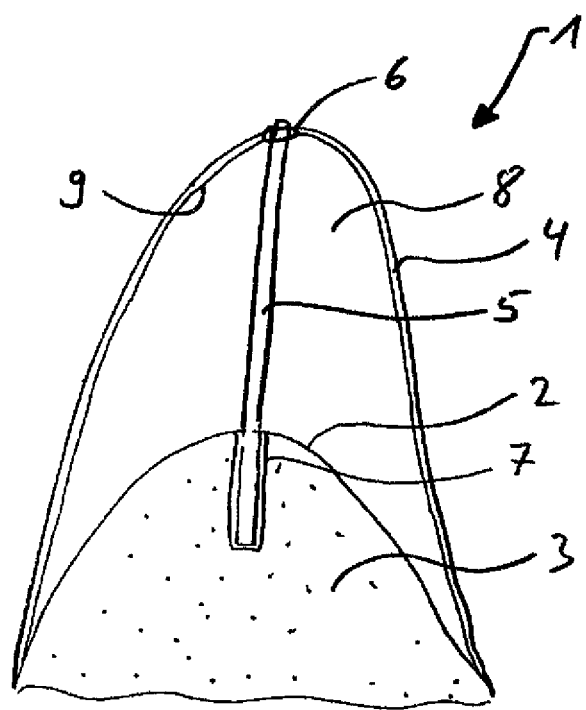

| | | | |
|---|---|---|---|
| 5,976,140 A | 11/1999 | Haas | |
| 5,984,966 A * | 11/1999 | Kiema et al. | 623/13.14 |
| 2004/0024466 A1 | 2/2004 | Heerklotz et al. | |
| 2004/0138591 A1* | 7/2004 | Iseki et al. | 600/587 |
| 2004/0143344 A1 | 7/2004 | Malaviya et al. | |
| 2006/0094951 A1* | 5/2006 | Dean et al. | 600/407 |
| 2008/0177334 A1* | 7/2008 | Stinnette | 606/304 |
| 2009/0234459 A1* | 9/2009 | Sporring et al. | 623/18.11 |
| 2011/0151400 A1* | 6/2011 | Boiangiu et al. | 433/76 |

FOREIGN PATENT DOCUMENTS

| | | |
|---|---|---|
| DE | 43 02 708 | 8/1994 |
| DE | 195 20 864 | 12/1996 |
| DE | 198 30 992 | 1/2000 |
| DE | 198 30 992 A1 | 1/2000 |
| DE | 10 2005 039 382 | 2/2007 |
| DE | 10 2005 041 412 | 3/2007 |
| DE | 10 2005 041 412 A1 | 3/2007 |
| DE | 10 2005 060 761 | 6/2007 |
| DE | 10 2005 060 761 A1 | 6/2007 |
| DE | 10 2006 047 054 | 4/2008 |
| DE | 10 2006 047 054 A1 | 4/2008 |
| EP | 0 809 979 | 12/1997 |
| WO | 01/91818 A1 | 12/2001 |
| WO | WO 01/91818 | 12/2001 |
| WO | 2006/051401 A2 | 5/2006 |
| WO | WO 2010/019463 | 2/2010 |

OTHER PUBLICATIONS

English translation of International Preliminary Report on Patentability and Written Opinion of the International Searching Authority in PCT/DE2011/000131, Aug. 21, 2012.

* cited by examiner

DEVICE FOR COVERING AND/OR RECONSTRUCTING A BONE DEFECT SITE, AND METHOD FOR PRODUCTION THEREOF

CROSS REFERENCE TO RELATED APPLICATIONS

This application is the National Stage of PCT/DE2011/000131 filed on Feb. 14, 2011, which claims priority under 35 U.S.C. §119 of German Application No. 10 2010 009 333.5 filed on Feb. 19, 2010 and German Application No. 10 2010 049 809.2 filed on Oct. 21, 2010, the disclosures of which are incorporated by reference. The international application under PCT article 21(2) was not published in English.

STATE OF THE ART

The invention proceeds from a device for covering and/or reconstruction of a bone defect site and from a method for the production of a cap of a covering device for a bone defect site.

Bone defect sites in the form of recesses or hollowed-out areas in the body's own bone tissue are often filled with bone augmentation material in bone surgery, for example in the reconstruction of bone in orthopedic, neurosurgical, or plastic surgery, or in maxillofacial surgery operations. In general, the bone augmentation material consists of a mixture of synthetic bone replacement material (for example hydroxyl apatite granulate) and natural bone particles. In order for osseous growth through the bone augmentation material to take place essentially exclusively from the bone side, the recess is closed off with a covering membrane, as described in the patent document DE 43 02 708 C2. The covering membrane is attached to the body's own bone using attachment nails, whereby the attachment process requires a maximum degree of technical skill of the surgeon, because the covering membrane consists of a flexible material.

In order to overcome this disadvantage of a lack of support function of the covering membrane, a covering membrane is described in the patent document U.S. Pat. No. 4,816,339, which consists of multiple layers, whereby these layers do not consist of absorbable membrane material. In this connection, it might be required that after the bone defect has healed, a second operation is necessary to remove material that is foreign to the body.

In the patent document DE 10 2005 039 382 54, a biodegradable hollow body that particularly has the shape of a hollow cylinder or conical cylinder is proposed. The hollow body has a plurality of openings on its walls, through which take-in of blood and therefore the growth of the body's own bone is possible. It is disadvantageous, in this connection, that in order to insert the hollow body, a cylindrical bore must be introduced into the existing bone, by means of a drill.

In the Offenlegungsschrift [unexamined patent application published for public scrutiny] DE 10 2006 047 054 A1, an implant socket is proposed, which is characterized by great fit precision and stability, so that the treating physician can handle and implant it in simple manner. The implant socket, which is made from hydroxyl apatite, and has a thin membrane, particularly one consisting of absorbable material, for protection of the mucous membrane from mechanical effects and for protection of the implant socket from tissue growing into it on the part of the mucous membrane, on the side facing the mucous membrane, is produced using an augmenting production method, so that the material composition forms a "gradient structure" in the sense of a decreasing density, particularly toward the inside. In this connection, a method of construction having a particularly porous structure is provided on the side facing the bone, and a compact method of construction is provided on the outside of the implant socket, on which a structure for holding a tooth implant and/or a tooth replacement is situated.

THE INVENTION AND ITS ADVANTAGES

The device according to the invention, for covering and/or reconstruction of a bone defect site, whereby the term "bone defect site" refers to a site of a (diseased) bone that deviates from the shape of a healthy bone, and the method according to the invention, for the production of a cap of a covering device for a bone defect site, in contrast, have the advantage that the device for covering and/or reconstruction of a bone defect site consists of a cap (for example a molded shell, rigid shell, molded body) and at least one fixation means for fixation of the cap on a bone, whereby the cap is characterized by a shape-stable (rigid) composition, and a wall of the cap that faces the bone defect or a wall of the cap that faces away from the bone defect corresponds to the shape of the regenerated bone, which once again has the shape of a healthy bone, as the result of its regeneration.

According to an advantageous embodiment of the device according to the invention, the cap and/or the fixation means consist, at least in part, of a biocompatible material. The biocompatible material can be biotolerant, bioinert and/or bioactive.

According to an embodiment of the device according to the invention that is advantageous in this regard, the biocompatible material is, at least in part, an autogenic, syngenic, allogenic, xenogenic, synthetic, or alloplastic material.

According to an additional advantageous embodiment of the device according to the invention, the cap and/or the fixation means consist, at least in part, of a biodegradable material.

According to an additional advantageous embodiment of the device according to the invention, the cap and/or the fixation means can consist, at least in part, of an absorbable material. Advantageously, the absorption time of the rigid shell can be controlled by means of its absorption gradients, and/or the absorption time can also amount to less than six months, so that the implant can be placed in timely manner.

According to an additional advantageous embodiment of the device according to the invention, the cap and/or the fixation means consist, at least in part, of a polymer or a polymer compound.

According to an additional advantageous embodiment of the device according to the invention, the cap and/or the fixation means consist, at least in part, of polylactide. Polylactides are composed of many lactic acid molecules chemically bound to one another, and belong to the polymers. The advantage of polylactide plastics, which are also called polylactic acids (PLA), is that they are plastics that are deformable by supplying heat, and are biocompatible.

According to an additional advantageous embodiment of the device according to the invention, the cap has a constant or varying wall thickness.

According to an embodiment of the device according to the invention that is advantageous in this regard, the wall thickness should amount to at least 0.2 mm, preferably 0.5 mm, but at least to an amount that shape stability of the molded shell results.

According to an additional advantageous embodiment of the device according to the invention, the fixation means is a pin, a screw, a nail and/or a bone adhesive.

According to an additional advantageous embodiment of the device according to the invention, the cap has at least one milled region (bore for the fixation means).

According to an embodiment of the device according to the invention that is advantageous in this regard, the milled region corresponds to the fixation means.

According to an additional advantageous embodiment of the device according to the invention, the wall that faces the bone defect demonstrates surface conditioning.

According to an embodiment of the device according to the invention that is advantageous in this regard, the surface can have a microstructure, pores, osteoblast attraction substances, means for promoting bone growth, and/or bone replacement material that contains BMP.

According to an advantageous embodiment of the method according to the invention, for the production of a cap of a covering device for a bone defect site, in which the computer-assisted design (CAD) of the cap is combined with computer-assisted manufacturing (CAM), as CAD/CAM, so that a design model of the cap developed on the computer is transmitted directly electronically to production, consisting of the following method steps:
- recording of a data set, which represents the affected bone defect site in its three-dimensionality, by means of tomography or similar imaging methods,
- use of the data set for planning of the cap, which has a wall that faces away from the bone defect and a wall that faces the bone defect, and can be fixed in place on a bone with at least one fixation means,
- implementation of the planning of the cap as a planning data set, and
- provision of the planning data set to a computer-controlled production method, wherein the cap is formed from a shape-stable material and its wall that faces the bone defect or its wall that faces away from the bone defect corresponds to the shape of the regenerated bone, and recording of the data set that represents the affected bone defect site in its three-dimensionality takes place by means of computer tomography or digital volume tomography.

According to an additional advantageous embodiment of the method according to the invention for the production of a cap of a covering device for a bone defect site, the cap is formed by means of milling, in the production process.

According to an additional advantageous embodiment of the method according to the invention for the production of a cap of a covering device for a bone defect site, a cleaning and/or sterilization process is carried out after production of the cap.

According to an additional advantageous embodiment of the method according to the invention for the production of a cap of a covering device for a bone defect site, the cap can be used in a device for covering and/or reconstruction of a bone defect site. In this way, a device for covering and/or reconstruction of a bone defect site can be created, the cap and/or fixation means of which, for example, of an artificial material and/or of a material of autogenic, synergenic, allogenic or xenogenic origin human and/or animal bone or the human, animal, or synthetic matrix a shape by means of which the region situated between the bone and the desired shape of the regenerated bone is completely or almost completely filled. For this purpose, a bone block is removed from the donor, for example, and subsequently modeled by means of CAD/CAM, if applicable.

Further advantages and advantageous embodiments of the invention can be derived from the following description, the drawing, and the claims.

DRAWING

Exemplary embodiments of the object of the invention are shown in the drawing and explained in greater detail in the following.

Figure 2:
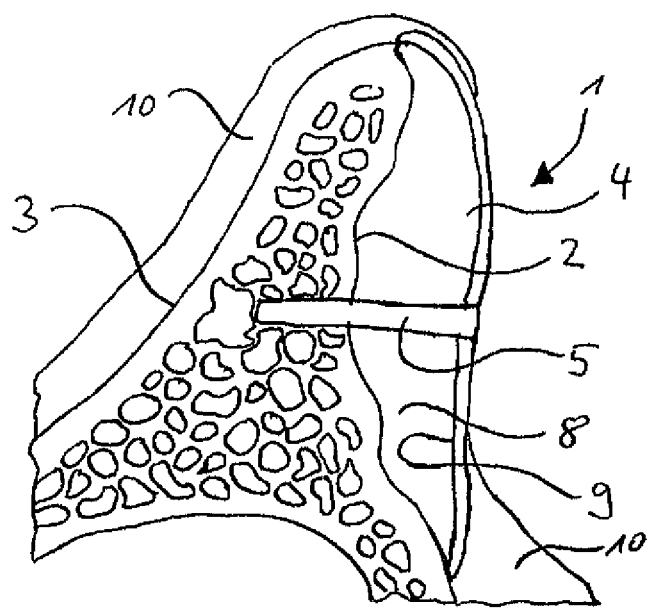
Figure 3:
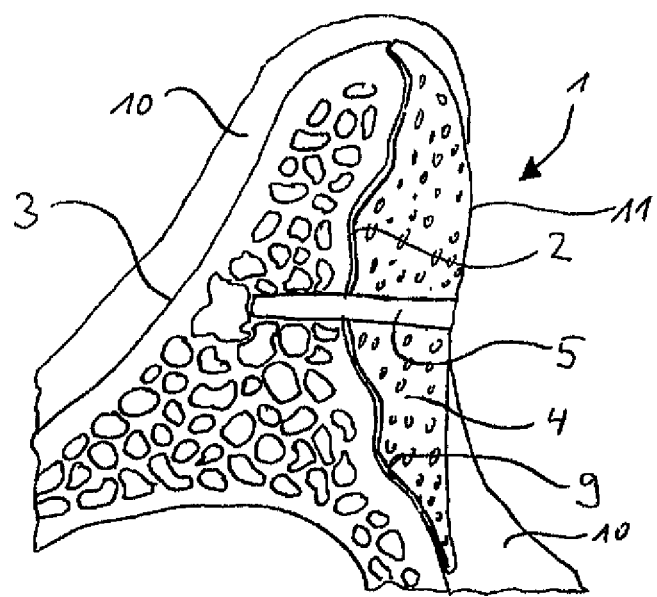
Figure 4:
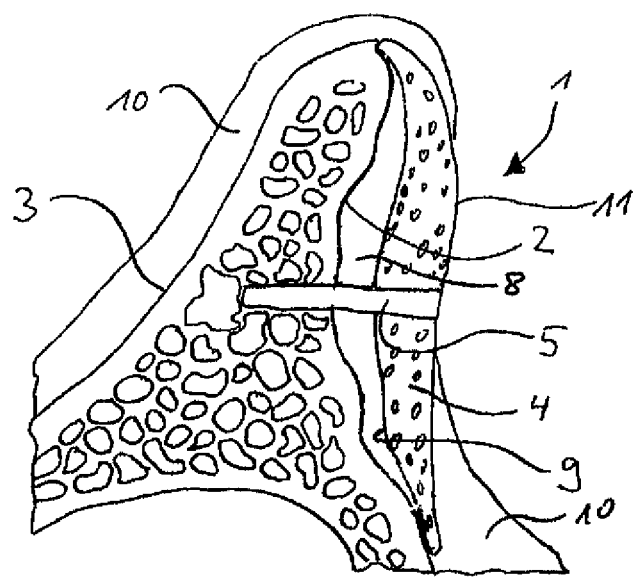

The figures show:

FIG. 1 a representation of a device according to the invention, for covering and/or reconstruction of a bone defect site, FIG. 2 a representation of a device according to the invention, for covering and/or reconstruction of a bone defect site, having a different shape, FIG. 3 a representation of a device according to the invention, for covering and/or reconstruction of a bone defect site, having a different shape, and FIG. 4 a representation of a device according to the invention, for covering and/or reconstruction of a bone defect site, having a different shape.

DESCRIPTION OF THE EXEMPLARY EMBODIMENT

FIG. 1 shows a representation of a device 1 according to the invention, for covering and/or reconstruction of a bone defect site 2 (bone defect) of a bone, particularly of a jaw bone 3. The device 1 consists of a cap 4 and a fixation means 5, which is shown as a pin in FIG. 1. The cap 4 is made of a shape-stable material, so that it supports itself and no additional support is required. For fixation of the cap 4 (molded shell, rigid shell), the fixation means 5 is pushed through a bore 6, into the cap 4, and subsequently introduced into the bore 7 disposed in the jaw bone 3. The subsequent fixation of the cap 4 takes place by means of ultrasound welding. During ultrasound welding, an ultrasound generator preferably generates a precisely defined frequency that is bundled by way of a sonotrode. After the absorbable fixation means 5 (pin) has been set onto a bore hole pre-drilled in the bone (bore 7), a vibration that is produced ensures liquefaction of the pin surface at its edges, thereby bringing about the result that the pin slides into the bore hole. By means of a change in the aggregate condition, the pin also penetrates into the osseous cavities that cannot be reached by a conventional bone screw, so that great initial strength is achieved. Furthermore, the pin head connects to the cap 4 and ensures a stable three-dimensional construct with a locking mechanism. During ultrasound welding, the fixation means 5 is therefore softened, so that it connects to the jaw bone 3 and the cap 4. By means of the cap 4, which has been fixed in place, a sealed interior space 8 is formed between the jaw bone 3 and the cap 4, which space is filled by means of the regeneration of the bone and/or by means of the introduction of autogenic, syngenic, allogenic, xenogenic, synthetic and/or alloplastic material, so that the regenerated bone or the introduced material corresponds to the shape of the wall 9 of the cap 4 that faces the bone defect site 2. In order to accelerate the regeneration process of the jaw bone 3, the wall 9 of the cap 4 that faces the bone defect can have a surface conditioning (for example microstructuring, pores, osteoblast attraction substances, means for promoting bone growth, and/or bone replacement materials that contain BMP).

FIG. 2 shows a representation of a device 1 according to the invention for covering and/or reconstruction of a bone defect site 2 (bone defect) of a bone, particularly of a jaw bone 3, having a different shape. In this figure, the gums 10 are additionally shown.

FIG. 3 shows a representation of a device 1 according to the invention for covering and/or reconstruction of a bone defect site 2 (bone defect) of a bone, particularly of a jaw bone 3, having a different shape. In this figure, the cap 4 is formed as a molded body, for example from human or animal bone, and has a wall 9 that faces the bone defect, which is adapted to the relief of the bone defect site 2, and a wall 11 that faces away from the bone defect, which corresponds to the shape of the regenerated bone.

FIG. 4 shows a representation of a device 1 according to the invention for covering and/or reconstruction of a bone defect site 2 (bone defect) of a bone, particularly of a jaw bone 3, having a different shape. In this figure, the cap 4 is formed as a molded body, for example from human or animal bone, and has a wall 9 that faces the bone defect and a wall 11 that faces away from the bone defect, which corresponds to the shape of the regenerated bone. An interior space 8 is situated between the wall 9 and the bone defect site 2, which space is filled by means of the regeneration of the bone and/or by means of the introduction of autogenic, syngenic, allogenic, xenogenic, synthetic and/or alloplastic material.

All the characteristics presented here can be essential to the invention both individually and in any desired combination with one another.

REFERENCE NUMBER LIST 1 device
2 bone defect site
3 jaw bone
4 cap
5 fixation means
6 bore
7 bore
8 interior space
9 wall
10 gums
11 wall

The invention claimed is:

1. A device comprising
    a cap consisting of a rigid material in a single layer and having a first wall adapted to face away from a bone defect when the device is in use, and having a second wall adapted to face the bone defect when the device is in use, and
    at least one fixation device adapted to fix the cap on a bone defect when the device is in use,
    wherein the entire second wall of the cap or the entire first wall of the cap is adapted to correspond to a shape of the bone following regeneration.

2. The device according to claim 1, wherein at least one of the cap and the fixation device comprises, at least in part, a biocompatible material.

3. The device according to claim 2, wherein the biocompatible material is, at least in part, an autogenic, syngenic, allogenic, xenogenic, synthetic, or alloplastic material.

4. The device according to claim 1, wherein at least one of the cap and the fixation device comprises, at least in part, a biodegradable material.

5. The device according to claim 1, wherein at least one of the cap and the fixation device comprises, at least in part, an absorbable material.

6. The device according to claim 1, wherein at least one of the cap and the fixation device comprises, at least in part, a polymer or a polymer compound.

7. The device according to claim 1, wherein at least one of the cap and the fixation device comprises, at least in part, of polylactide.

8. The device according to claim 1, wherein the cap has a varying wall thickness.

9. The device according to claim 8, wherein the wall thickness amounts to at least 0.2 mm.

10. The device according to claim 1, wherein the fixation device is at least one of a pin, a screw, a nail, and a bone adhesive.

11. The device according to claim 1, wherein the bore of the cap comprises a milled region.

12. The device according to claim 1, wherein the second wall demonstrates surface conditioning.

13. The device according to claim 12, wherein the surface conditioning has at least one of a microstructure, pores, osteoblast attraction substances, bone growth promoters, and a bone replacement material that contains a bone morphogenetic protein.

14. The device according to claim 1, wherein the cap comprises a bore,
    wherein the at least one fixation device protrudes through the bore of the cap to allow the at least one fixation device to fix the cap on the bone defect when the device is in use, and
    wherein a surface of the at least one fixation device faces away from the bone defect when the device is in use and is disposed flush with the first wall of the cap.

15. A method for producing a cap adapted to cover a bone defect site comprising the following method steps:
    using an imaging method to record a data set comprising a three-dimensional representation of an affected bone defect site,
    using the data set to create a planning data set to plan production of the cap wherein the cap has a first wall adapted to face away from bone defect when in use and a second wall adapted to face the bone defect when in use, and wherein the cap is adapted to be fixed in place on a bone defect with at least one fixation device when in use, and
    providing the planning data set to a computer-controlled production method, the computer-controlled production method producing the cap,
    wherein the entire second wall or the entire first wall of the cap are adapted to correspond to a shape of the bone following regeneration, and
    wherein the cap consists of a rigid material in a single layer.

16. The method for producing a cap according to claim 15, wherein the imaging method comprises computer tomography or digital volume tomography.

17. The method for producing a cap according to claim 15, wherein the cap is formed by milling during production.

18. The method for producing a cap according to claim 15, wherein after production of the cap at least one of a cleaning process and a sterilization process is carried out.

19. A method for covering and/or reconstruction of a bone defect comprising:
    (a) providing a device comprising a cap, the cap consisting of a rigid material in a single layer, the cap having a first wall adapted to face away from a bone defect when the device is in use, and the cap having a second wall adapted to face the bone defect when the device is in use, and the device comprising at least one fixation device adapted to fix the cap on a bone defect when the device is in use; and
    (b) covering a bone defect site with the cap and fixing the cap by ultrasound welding the at least one fixation device to the bone defect to form a sealed interior space between the bone defect site and the cap, the entire second wall of the cap or the entire first wall of the cap being adapted to correspond to a shape of the bone following regeneration.

* * * * *